United States Patent
Brugmans et al.

(10) Patent No.: US 10,834,881 B2
(45) Date of Patent: Nov. 17, 2020

(54) TOMATO PLANTS WITH IMPROVED DISEASE RESISTANCE

(71) Applicant: SEMINIS VEGETABLE SEEDS, INC., St. Louis, MO (US)

(72) Inventors: Bart Willem Brugmans, Beek en Donk (NL); Derek R. Drost, Penn Valley, CA (US); Albert Grit, Ermelo (NL); Jacobus Hoogstraten, Wageningen (NL); Maria Fernanda Rodriguez, St. Louis, MO (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 0 days.

(21) Appl. No.: 16/425,747

(22) Filed: May 29, 2019

(65) Prior Publication Data

US 2019/0373831 A1    Dec. 12, 2019

Related U.S. Application Data

(62) Division of application No. 14/882,384, filed on Oct. 13, 2015, now Pat. No. 10,368,508.

(60) Provisional application No. 62/064,375, filed on Oct. 15, 2014.

(51) Int. Cl.
*A01H 5/08*     (2018.01)
*C12Q 1/68*     (2018.01)
*A01H 1/04*     (2006.01)

(52) U.S. Cl.
CPC ................ *A01H 5/08* (2013.01); *A01H 1/04* (2013.01)

(58) Field of Classification Search
None
See application file for complete search history.

(56) References Cited

U.S. PATENT DOCUMENTS

| 6,414,226 | B1 | 7/2002 | Hoogstraten |
| 8,785,720 | B2 | 7/2014 | Hoogstraten et al. |
| 2014/0208459 | A1 | 7/2014 | Bai et al. |

FOREIGN PATENT DOCUMENTS

| EP | 1563727 | | 8/2005 |
| RU | 2020802 | C1 | 10/1994 |
| WO | WO 2012/125025 | | 9/2012 |
| WO | WO 2013/135726 | | 9/2013 |
| WO | WO 2014/104878 | | 7/2014 |

OTHER PUBLICATIONS

Verlaan et al., 2013, The Tomato Yellow Leaf Curl Virus Resistance Genes Ty-1 and Ty-3 Are Allelic and Code for DFDGD-Class RNA-Dependent RNA Polymerases, PLOS Genetics 9: 1-11.*
Extended European Search Report regarding European Application No. 15851041.2, dated Mar. 26, 2018.
Eybishtz et al., "tomato yellow leaf curl virus infection of a resistant tomato line with a silenced sucrose transporter gene LeHT1 results in inhibition of growth, enhanced cirus spread, and necrosis," *Planta*; 231:537-548; 2010.
Gonzalex-Cabezuelo et al., "Genotyping selection for resistance against tomato yellow leaf curl virus (TYLCV) conferred by Ty-1 and Ty-3 genes in tomato," *Mol Breeding* doi: 10.1007/s11032-012-9701-3, 2012.
Groenewegen et al., "Natural Cross Pollination in California Commercial Tomato Fields," *HortSci*; 29(9); 1088; 1994.
Hutton et al., "Recessive resistance to tomato yellow leaf curl virus from the tomato cultivar tyking is located in the same region as Ty-5 on Chromosome 4," *HortScience*, 47(3):324-327, 2012.
International Search Report and Written Opinion for International Application No. PCT/US2015/055339, dated Mar. 2, 2016.
Ji et al., "Ty-3, a begomovirus resistance locus near the Tomato yellow leaf curl virus resistance locus Ty-1 on chromosome 6 of tomato," *Mol. Breeding* 20:271-284, 2007.
Ji et al., "Toward fine mapping of the tomato yellow leaf curl virus resistance gene Ty-2 on chromosome 11 of tomato," *HortScience*, 44(3):614-618, 2009.
Lin et al., "Genomic analyses provide insights into the history of tomato breeding," *Nature Genetics* 46(11):1220-1226, 2014.
Solanum chilense accession LA1969, Ty-1; Tomato Genetics Resource Center accession year 1979.
Verlaan et al. "The Tomato Yellow Leaf Curl Virus Resistance Genes Ty-1 and Ty-3 Are Allelic and Code for DFDGD-Class RNA-Dependent RNA Poiymerases," *PLOS Genetics* 9(3):e1003399, 2013.
Verlaan et al., "Chromosomal rearrangements between tomato and *Solanum chilense* hamper mapping and breeding of the TYLCV resistance gene Ty-1," *The Plant Journal* 68:1093-1103, 2011.
Vidavsky et al., "Tomato breeding lines resistant and tolerant to tomato yellow leaf curl virus issued from *Lycopersicon hirsutum*," *Phytopathology*, 88(9):910-914, 1998.

* cited by examiner

*Primary Examiner* — Bratislav Stankovic
(74) *Attorney, Agent, or Firm* — Dentons US LLP; Matthew L. Madsen, Esq.

(57) ABSTRACT

The present disclosure provides tomato plants exhibiting resistance to tomato yellow leaf curl virus (TYLCV) and lacking unfavorable linked traits such as necrosis. Such plants may comprise novel introgressed genomic regions associated with disease resistance from *S. chilense*. In certain aspects, compositions, including novel polymorphic markers and methods for producing, breeding, identifying, and selecting plants or germplasm with a disease resistance phenotype are provided.

15 Claims, 10 Drawing Sheets

Specification includes a Sequence Listing.

FIG. 1

| | 1 | | | | 2 | | | | | 3 | | | 4 | | | | | | | |
|---|---|---|---|---|---|---|---|---|---|---|---|---|---|---|---|---|---|---|---|---|
| | Mi | C2-At4g0 1930 | Q-NL51 13480 | Q-NL51 13524 | CD267 301 | 9K0 1 | SP6 | NL02 16601 | NL02 16387 | NL02 32354 | NL02 15181 | T19 655 | NL51 1853 | NL51 1852 | TyE asy gene ns0e | Ty3 T0 5506 | NL51 13407 | Ty3 T1 04679 | Ty1 Phe not ype | TYLCV Agro Pro res ist an ce | TYLCV field res ist an ce | Leaf |
| original | c | c | c | c | c | c | c | c | c | c | c | c | c | c | c | c | c | c | R | Yes |
| Ty/Mi | p | nd | nd | nd | c | c | c | c | c | c | c | c | c | c | c | c | c | c | R | Yes |
| 11039-1 | p/e | | c | c/e | c/e | c/e | c/e | c/e | c/e | c/e | c/e | e | e | e | e | e | e | e | S | Yes |
| 09GA0361-11 | p | e | e | e | e | c | c | c | c | c | c | c | c | c | c | c | c | c | R | Reduced |
| 08TK01-26-2 | e | e | e | e | e | e | e | e | e | e | e | e | e | e | c/e | c/e | c/e | c/e | e | nd | R | nd |

Legend

| trait conferred | allelic composition | |
|---|---|---|
| | esculentum | e |
| nematode | peruvianum | p |
| | peruvianum/esculentum | p/e |
| geminivirus | chilense | c |
| | chilense/esculentum | c/e | nd = no data

FIG. 3

| average necrosis April | average necrosis May | | NL0232061 | NL0216350 | NSLYC005134405 | NL0244835 | NSLYC005134413 | NSLYC005134429 | NSLYC008382908 | NSLYC008373232 | NSLYC009078368 |
|---|---|---|---|---|---|---|---|---|---|---|---|
| | | | 4.32 | 4.25 | 6.4 | 7.47 | 7.88 | 8.23 | 8.51 | 8.93 | 9.14 |
| | | | 21,597,226 | 27,605,333 | | 29,785,303 | 30,027,432 | 30,199,948 | 30,322,811 | 30,523,713 | 30,623,862 |
| 1 | 1 | S-parent | esc | esc | esc | esc | esc | esc | esc | esc | esc |
| 8 | 8 | R-parent | chi | chi | chi | chi | chi | chi | chi | chi | chi |
| 4 | 2 | Hybrid | heterozygote | heterozygote | heterozygote | heterozygote | heterozygote | heterozygote | heterozygote | heterozygote | heterozygote |
| 8 | 7 | family-1 | chi | chi | chi | chi | chi | chi | chi | chi | chi |
| 8 | 8 | family-2 | chi | chi | chi | chi | chi | chi | chi | chi | chi |
| 2 | 2 | family-3 | esc | esc | esc | esc | esc | esc | esc | esc | esc |
| 3 | 2 | family-4 | esc | esc | esc | esc | esc | esc | esc | esc | esc |
| 2 | 2 | family-5 | esc | esc | esc | esc | esc | esc | esc | esc | esc |
| 1 | 1 | family-6 | esc | esc | esc | esc | esc | esc | esc | esc | esc |
| 1 | 2 | family-7 | esc | esc | esc | esc | esc | esc | esc | esc | chi |
| 2 | 1 | family-8 | esc | esc | esc | esc | esc | esc | esc | esc | chi |
| 1 | 2 | family-9 | esc | esc | esc | esc | esc | esc | esc | chi | chi |
| 1 | 1 | family-10 | esc | esc | esc | esc | esc | esc | chi | chi | chi |
| 2 | 1 | family-11 | esc | esc | esc | esc | esc | chi | chi | chi | chi |
| 4 | 4 | family-12 | esc | esc | esc | esc | esc | chi | chi | chi | chi |
| 8 | 8 | family-13 | esc | esc | esc | esc | esc | chi | chi | chi | chi |
| 4 | 3 | family-14 | esc | esc | esc | esc | chi | chi | chi | chi | chi |
| 7 | 7 | family-15 | esc | esc | esc | esc | chi | chi | chi | chi | chi |
| 3 | 4 | family-16 | esc | esc | esc | esc | chi | chi | chi | chi | chi |
| 6 | 6 | family-17 | esc | esc | esc | esc | chi | chi | chi | chi | chi |
| 4 | 4 | family-18 | esc | esc | esc | chi | chi | chi | chi | chi | chi |
| 3 | 3 | family-19 | esc | esc | esc | chi | chi | chi | chi | chi | chi |
| 2 | 2 | family-20 | esc | esc | esc | chi | chi | chi | chi | chi | chi |
| 3 | 3 | family-21 | esc | esc | esc | chi | chi | chi | chi | chi | chi |
| 2 | 2 | family-22 | esc | esc | esc | chi | chi | chi | chi | chi | chi |
| 4 | 4 | family-23 | esc | esc | chi | chi | chi | chi | chi | chi | chi |
| 2 | 3 | family-24 | esc | esc | chi | chi | chi | chi | chi | chi | chi |
| 6 | 5 | family-25 | esc | chi | chi | chi | chi | chi | chi | chi | chi |
| 9 | 9 | family-26 | chi | chi | chi | chi | chi | chi | chi | chi | chi |
| 7 | 5 | family-27 | chi | chi | chi | chi | chi | chi | chi | chi | chi |
| 9 | 8 | family-28 | chi | chi | chi | chi | chi | chi | chi | chi | chi |
| 8 | 8 | family-29 | chi | chi | chi | chi | chi | chi | chi | chi | chi |

FIG. 5

| family | MRN genetic position physical position | Chr. 6 NL0232061 4.32 21,597,226 | NL0216350 4.25 27,605,333 | NL0244835 7.47 29,785,303 | NSLYC005134413 7.88 30,027,432 | NSLYC005134429 8.23 30,199,948 | NSLYC008382908 8.51 30,322,811 | NSLYC008373232 8.93 30,523,713 | NSLYC009078368 9.14 30,623,862 | NSLYC009077969 9.21 30,658,888 | NSLYC009077970 9.27 30,689,718 | Ty-1 region NSLYC008383071 9.31 30,711,829 | NSLYC009418370 9.64 30,876,429 | NSLYC008426177 9.67 30,892,169 | NL231193 11.6 31,800,043 | Chr. 2 NSLYC008374675 39 chr 2 | NSLYC008375578 59.6 chr 2 | necrosis may |
|---|---|---|---|---|---|---|---|---|---|---|---|---|---|---|---|---|---|---|
| 14TJD0003-7 | 13 | AA | AA | AACCAACC | | | | | | | | TT | ** | TT | AA | TT | GG | 2 |
| 14TJD0010-1 | 17 | AA | AA | AACCAACC | | | | | | | | TT | ** | TT | AA | TT | GG | 4 |
| 14TJD0010-2 | 19 | AA | AA | AACCAACC | | | | | | | | TT | ** | TT | AA | TT | GG | 3 |
| 14TJD0010-3 | 21 | AA | AA | AACCAACC | | | | | | | | TT | ** | TT | AA | TT | GG | 2 |
| 14TJD0010-15 | 23 | AA | AA | AACCAACC | | | | | | | | TT | ** | TT | AA | TT | GG | 2 |
| 14TJD0020-2 | 28 | AA | | ******** | TT | TT | GG | CC | CC | GG | TT | TT | ** | TT | AA | TT | GG | 1 |
| 14TJD0020-3 | 30 | GG | | AACCAACC | AA | ** | GG | CC | CC | GG | TT | TT | ** | TT | AA | TT | GG | 8 |
| 14TJD0020-4 | 32 | AA | | ******** | TT | TT | GG | CC | CC | GG | TT | TT | ** | TT | AA | TT | GG | 1 |
| 14TJD0020-5 | 33 | GG | | AACCAACC | AA | ** | GG | CC | CC | GG | TT | TT | ** | TT | AA | TT | GG | 8 |
| 14TJD0020-9 | 35 | GG | | AACCAACC | AA | ** | GG | CC | CC | GG | TT | TT | ** | TT | AA | TT | GG | 8 |
| 14TJD0020-10 | 37 | GG | | AACCAACC | AA | ** | GG | CC | CC | GG | TT | TT | ** | TT | AA | TT | GG | 8 |
| 14TJD0020-12 | 39 | AA | | ******** | TT | TT | GG | CC | CC | GG | TT | TT | ** | TT | AA | TT | GG | 1 |
| 14TJD0021-1 | 41 | AA | | ******** | TT | TT | AA | TT | AA | AA | GG | TT | ** | TT | AA | TT | GG | 1 |
| 14TJD0021-3 | 43 | GG | | AACCAACC | AA | ** | GG | CC | CC | GG | TT | TT | ** | TT | AA | TT | GG | 8 |
| 14TJD0021-4 | 45 | AA | | ******** | TT | - | AA | TT | AA | AA | GG | TT | ** | TT | AA | TT | GG | 2 |
| 14TJD0021-6 | 47 | AG | | AACC**** | AT | T/* | AA | CT | AC | AG | GT | TT | ** | TT | AA | TT | GG | 4 |
| 14TJD0021-8 | 34 | GG | | AACCAACC | AA | ** | GG | CC | CC | GG | TT | TT | ** | TT | AA | TT | GG | 8 |
| 14TJD0021-12 | 36 | GG | | AACCAACC | AA | ** | GG | CC | CC | GG | TT | TT | ** | TT | AA | TT | GG | 8 |
| 14TJD0021-13 | 38 | AA | | ******** | TT | TT | AA | TT | AA | AA | GG | TT | ** | TT | AA | TT | GG | 2 |
| 14TJD0021-15 | 40 | GG | | AACCAACC | AA | ** | GG | CC | CC | GG | TT | TT | ** | TT | AA | TT | GG | 9 |
| 14TJD0028-2 | 53 | AA | | ******** | AA | ** | GG | CC | CC | GG | TT | TT | ** | TT | AA | TT | GG | 2 |
| 14TJD0030-11 | 52 | AA | | ******** | AA | ** | GG | CC | CC | GG | TT | TT | ** | TT | AA | TT | GG | 2 |
| 14TJD0002-4 | 3 | AA | AA | AACCAACC | | | | | | | | TT | ** | TT | AA | CC | AA | 4 |
| 14TJD0003-4 | 9 | AA | AA | AACCAACC | | | | | | | | TT | ** | TT | AA | CC | AA | 9 |
| 14TJD0007-5 | 8 | AA | AA | ******** | TT | ** | GG | - | CC | GG | TT | TT | ** | TT | AA | CC | AA | 5 |
| 14TJD0013-13 | 31 | AA | AA | ******** | | | | | | | | CC | TT | AA | CC | CC | AA | 5 |
| 14TJD0014-5 | 18 | GG | | AACCAACC | | | | | | | | TT | ** | TT | AA | CC | AA | 6 |
| 14TJD0014-16 | 26 | GG | | AACCAACC | AA | ** | GG | CC | CC | GG | TT | TT | ** | TT | AA | CC | AA | 3 |

FIG. 6

| ID | TYLCV phenotype | Q-NLO23206 1 | Q-NSLYC0057 0 4 0 0 6 0 8 | Q-NSLYC0051 3 4 4 2 9 | Q-NSLYC0090 7 8 3 6 8 | Q-NSLYC0090 7 8 1 6 9 | Q-NSLYC0090 7 7 9 6 9 | Q-NSLYC0090 7 7 9 0 | Q-NSLYC008384 3 6 1 2 | Q-NLO23 1 1 1 8 0 2 7 | Q-NLO23 1 1 1 9 3 |
|---|---|---|---|---|---|---|---|---|---|---|---|---|
|  |  | 20.040 | 32.030 | 32.390 | 32.763 | 32.766 | 32.798 | 32.828 | 32.850 | 32.987 | 33.280 | 33.920 |
| FIR-AY06074 | Resistant | GG | CC | ** | CC | AA | GG | TT | TT | CC | CC | AA |
| FDR-16-2133 | Resistant | GG | CC | ** | CC | AA | GG | TT | TT | CC | CC | AA |
| 11TTY0005_13 | Resistant | AA | CC | ** | CC | AA | GG | TT | TT | CC | CC | AA |
| 11TTY0005_16 | Resistant | AA | CC | ** | CC | AA | GG | TT | TT | CC | CC | AA |
| 11TTY0019_10 | Resistant | AA | TT | ** | CC | AA | GG | TT | TT | CC | CC | AA |
| 11TTY0059_02 | Resistant | AA | TT | ** | CC | AA | GG | TT | TT | CC | CC | AA |
| 11TTY0054_02 | Resistant | AA | TT | CC | CC | AA | GG | TT | TT | CC | CC | AA |
| 11TTY0054_10 | Resistant | AA | TT | CC | CC | AA | GG | TT | TT | CC | CC | AA |
| 11TTY0029_04 | Resistant | AA | TT | CC | AA | AA | GG | TT | TT | CC | CC | AA |
| 11TTY0029_13 | Resistant | AA | TT | CC | AA | AA | GG | TT | TT | CC | CC | AA |
| 11TTY0064_04 | Resistant | AA | TT | CC | AA | GG | GG | TT | TT | CC | CC | AA |
| 11TTY0064_08 | Resistant | AA | TT | CC | AA | GG | GG | TT | TT | CC | CC | AA |
| 11TTY0018_01 | Susceptible | AA | TT | CC | AA | GG | AA | GG | CC | TT | CC | AA |
| 11TTY0052_15 | Susceptible | AA | TT | CC | AA | GG | AA | GG | CC | TT | CC | AA |
| 11TTY0014_06 | Susceptible | GG | CC | ** | CC | AA | GG | TT | CC | TT | TT | CC |
| 11TTY0048_16 | Susceptible | GG | CC | ** | CC | AA | GG | TT | CC | TT | TT | CC |
| FIR-16-1078 | Susceptible | AA | TT | CC | AA | GG | AA | GG | CC | TT | TT | CC |
| FDR-16-0197 | Susceptible | AA | TT | CC | AA | GG | AA | GG | CC | TT | TT | CC |

FIG. 7

| Chromosome | 6 | 6 | 6 | 6 | 6 | 6 | 6 | 6 | 6 |
|---|---|---|---|---|---|---|---|---|---|
| Marker | NSLYC008362808 | NSLYC008373232 | NSLYC009078368 | NSLYC008077968 | NSLCY008383071 | NSLYC009418370 | NSLYC008428177 | NL0231187 | NL0231193 |
| Genetic position (cM, v2.7.5) | 8.51 | 8.93 | 9.14 | 9.21 | 9.31 | 9.64 | 9.67 | 10.21 | 11.58 |
|  | 30,321,811 | 30,523,713 | 30,623,862 | 30,658,888 | 30,721,829 | 30,876,429 | 30,892,169 | 31,166,320 | 31,600,043 |
| FDR-15-2061 | ESC | CHI | CHI | CHI | CHI | CHI | CHI | CHI | CHI |
|  | ESC | ESC | CHI | CHI | CHI | CHI | CHI | CHI | CHI |
|  | ESC | ESC | ESC | CHI | CHI | CHI | CHI | CHI | CHI |
|  | ESC | ESC | ESC | ESC | CHI | CHI | CHI | CHI | CHI |
|  | ESC | ESC | ESC | ESC | ESC * | CHI | CHI | CHI | CHI |
| FDR-14-618 | ESC | CHI | CHI | CHI | CHI | CHI | CHI | CHI | CHI |
|  | ESC | ESC | CHI | CHI | CHI | CHI | CHI | CHI | CHI |
|  | ESC | ESC | ESC | CHI | CHI | CHI | CHI | CHI | CHI |
|  | ESC | ESC | ESC | ESC | CHI | CHI | CHI | CHI | CHI |

Set Ty1-3, FDR-GI14-0001 recombinant

| Means for Oneway ANOVA | | |
|---|---|---|
| Level | Mean | Student's t test (alpha = 0.05) |
| RC - RP | 32.38 | A |
| P - RP | 28.69 | A, B |
| RC - D | 27.81 | B |
| P - D | 22.94 | C |

| Ordered Differences Report | | | | | | |
|---|---|---|---|---|---|---|
| Level | - Level | Difference | Std Err Diff | Lower CL | Upper CL | p-Value |
| RC - RP | P - D | 9.44 | 1.73 | 5.67 | 13.20 | 0.0001 |
| P - RP | P - D | 5.75 | 1.73 | 1.99 | 9.51 | 0.0040 |
| RC - RP | RC - D | 5.06 | 1.73 | 1.30 | 8.83 | 0.0126 |
| RC - D | P - D | 4.38 | 1.73 | 0.61 | 8.14 | 0.0263 |
| RC - RP | P - RP | 3.69 | 1.73 | -0.08 | 7.45 | 0.0540 |
| P - RP | RC - D | 1.38 | 1.73 | -2.39 | 5.14 | 0.4414 |

Set Ty1-3, FDR-GI14-0001 recombinant

Means for Oneway ANOVA

| Level | Mean | Student's t test (alpha = 0.05) |
|---|---|---|
| P - D | 0.20 | A |
| RC - D | 0.17 | B |
| P - RP | 0.17 | B |
| RC - RP | 0.16 | B |

Ordered Differences Report

| Level | - Level | Difference | Std Err Diff | Lower CL | Upper CL | p-Value |
|---|---|---|---|---|---|---|
| P - D | RC - RP | 0.04 | 0.01 | 0.02 | 0.05 | 0.001 |
| P - D | P - RP | 0.03 | 0.01 | 0.01 | 0.04 | 0.0084 |
| P - D | RC - D | 0.03 | 0.01 | 0.01 | 0.04 | 0.0101 |
| RC - D | RC - RP | 0.01 | 0.01 | -0.01 | 0.03 | 0.2258 |
| P - RP | RC - RP | 0.01 | 0.01 | -0.01 | 0.03 | 0.2612 |
| RC - D | P - RP | 0.00 | 0.01 | -0.02 | 0.02 | 0.9237 |

SEQUENCE LISTING

```
<160> NUMBER OF SEQ ID NOS: 22

<210> SEQ ID NO 1
<211> LENGTH: 764
<212> TYPE: DNA
<213> ORGANISM: Solanum tomato
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (97)..(99)
<223> OTHER INFORMATION: n is a, c, g, or t
<220> FEATURE:
<221> NAME/KEY: misc_feature
<222> LOCATION: (102)..(104)
<223> OTHER INFORMATION: n is a, c, g, or t
<220> FEATURE:
<221> NAME/KEY: misc_feature
<222> LOCATION: (106)..(110)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (461)..(461)
<223> OTHER INFORMATION: n is a, c, g, or t
<220> FEATURE:
<221> NAME/KEY: misc_feature
<222> LOCATION: (520)..(520)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
```

```
<221> NAME/KEY: misc_feature
<222> LOCATION: (545)..(545)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t
<220> FEATURE:
<221> NAME/KEY: misc_feature
<222> LOCATION: (643)..(643)
<223> OTHER INFORMATION: n is a, c, g, or t
<220> FEATURE:
<221> NAME/KEY: misc_feature
<222> LOCATION: (655)..(655)
<223> OTHER INFORMATION: n is a, c, g, or t
<220> FEATURE:
<221> NAME/KEY: misc_feature
<222> LOCATION: (686)..(686)
<223> OTHER INFORMATION: n is a, c, g, or t
<220> FEATURE:
<221> NAME/KEY: misc_feature
<222> LOCATION: (698)..(698)
<223> OTHER INFORMATION: n is a, c, g, or t
<220> FEATURE:
<221> NAME/KEY: misc_feature
<222> LOCATION: (709)..(709)
<223> OTHER INFORMATION: n is a, c, g, or t

<400> SEQUENCE: 1
cataaccatg acacctcacc ttgaatttgt cgtgtcaatg catccntnac caaggctaat      60
aaaaaaggct aagggntgat tcntggtgca accccannna annngnnnnn tgctcagagt     120
ctcctcccag tgtccttaca tgagtattgg cttcatcata tataccctta ttttcctagt     180
gtaagccaca tntataacctc tagnctccaa tcaactccat agaaccttcc ttgggacttc     240
atggtaagcc ttctctaggt ggatgaatat catcggtaag tccttcgctt ccntatattg     300
ctccaccagt cttttttacga gatgaatgac ttctgtcatt caggccntga catgaatcta     360
aacaggtttt caaaaatagc cacgccccctc ctccctctaa tctccaccac cctctcccaa     420
accttcatat tgtagcttag cagcttgata cccttggtt nttgcaattt tagatgtcac     480
ccttgttcat gaacaacaaa atcattgtac ttcacctccn ttcttcaggc atcnttgtgt     540
ccnanaaacg acattaaaca actctgtcaa gcactccaca cctgccctgt ctgcnacctt     600
ccaaaattca actgggatct cgtctggccc agtcactcta ccnttatgcc agggncgaac     660
ctacatagtg tcaagagggt ccatangaac ccacttcnta aaaaaattna tattgtatat     720
ataggtagat ttggtttgtc ttctggacaa tacatgtata gata                      764

<210> SEQ ID NO 2
<211> LENGTH: 121
<212> TYPE: DNA
<213> ORGANISM: Solanum tomato

<400> SEQUENCE: 2
aaaccaattc acaacaaaga tgatgatatc ctttaactac tgtaaggcta gggagtacct      60
gtatttcaag ttatacggaa aacaatgcat cactccagtt gcaatcatga caagtgcagc     120
a                                                                      121

<210> SEQ ID NO 3
<211> LENGTH: 747
<212> TYPE: DNA
<213> ORGANISM: Solanum tomato
<220> FEATURE:
<221> NAME/KEY: misc_feature
<222> LOCATION: (59)..(59)
<223> OTHER INFORMATION: n is a, c, g, or t
```

-continued

```
<220> FEATURE:
<221> NAME/KEY: misc_feature
<222> LOCATION: (69)..(70)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (249)..(255)
<223> OTHER INFORMATION: n is a, c, g, or t
<220> FEATURE:
<221> NAME/KEY: misc_feature
<222> LOCATION: (277)..(277)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (414)..(415)
<223> OTHER INFORMATION: n is a, c, g, or t
<220> FEATURE:
<221> NAME/KEY: misc_feature
<222> LOCATION: (417)..(424)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (530)..(530)
<223> OTHER INFORMATION: n is a, c, g, or t
<220> FEATURE:
<221> NAME/KEY: misc_feature
<222> LOCATION: (685)..(685)
```

<223> OTHER INFORMATION: n is a, c, g, or t

<400> SEQUENCE: 3

| | | | | | |
|---|---|---|---|---|---|
| caatttctct | ttgttctcct | tgcttattta | taatcaaaat | catcagtaaa | caaaaaaant | 60 |
| aattaaacnn | aaatgtaacc | taaatnaact | naccttctcc | aaatcttctt | gtaaatatct | 120 |
| aacaanggag | gcaaccattt | atattttcca | ttttggtcnt | anattcccac | attttttctta | 180 |
| aaatacnttt | taggaattaa | tattancttc | tttatatgtg | caacatcttt | cacatatttt | 240 |
| gttatatann | nnnnnatata | tgagatttgt | ctacaantca | aagtaacaaa | atgttataaa | 300 |
| aaaaanctca | taagataatt | gaattttcct | atactccatc | atcaatccat | ngctaaatgg | 360 |
| gattaacntg | acatttttat | natntagcta | tgaaatttta | tctgtcgcta | attnngnnnn | 420 |
| nnnnagaaag | agatgatgat | atatacatac | cttaatagat | ggattggatg | aagaagcaga | 480 |
| aagaagtcca | gttattgttt | tattatcact | tcctttgta | ttttcaanan | gatcaacctt | 540 |
| gttggtagtc | aacgtaatta | ttgttctagc | tccttcgtaa | caagctgcac | atattgtatt | 600 |
| tcttggtggc | cttaaaataa | atggcatcgc | gctacatata | gaacaatcca | tatttatttg | 660 |
| tgcgcttcga | ttaattttt | tctgntcaat | attcgaagaa | gaaattactg | aactcaaatg | 720 |
| atcaatgaag | aagagacgat | gatcgat | | | | 747 |

```
<210> SEQ ID NO 4
<211> LENGTH: 338
<212> TYPE: DNA
<213> ORGANISM: Solanum tomato
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (29)..(31)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (139)..(139)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (202)..(203)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
```

```
<220> FEATURE:
<221> NAME/KEY: misc_feature
<222> LOCATION: (230)..(230)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (244)..(244)
<223> OTHER INFORMATION: n is a, c, g, or t
<220> FEATURE:
<221> NAME/KEY: misc_feature
<222> LOCATION: (253)..(253)
<223> OTHER INFORMATION: n is a, c, g, or t
<220> FEATURE:
<221> NAME/KEY: misc_feature
<222> LOCATION: (257)..(257)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (277)..(277)
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (284)..(285)
<223> OTHER INFORMATION: n is a, c, g, or t
<220> FEATURE:
<221> NAME/KEY: misc_feature
<222> LOCATION: (313)..(314)
<223> OTHER INFORMATION: n is a, c, g, or t

<400> SEQUENCE: 4
aagnattata aagatgcata canaataann nataccagag aatcaaaaca cttaaaaaga      60
cagatatgtt tttctatcat tctgttcctg cacnaaaagt aataaatttt gtaagcatnt     120
gttcttcaca aatgatatnc tccctccgtt gcaatttgtt tgtttgatat tnacttgana    180
cggagtttaa naaagtgaag anngcttttg aanattgtgg tcttgaaagn aatntgttga    240
attnaccaaa atntccntca ancttatggt nttaaanagn ctanntggaa agttaaaatt    300
aaatagttgt cannaaaagg aaagaggtct taaacatg                            338

<210> SEQ ID NO 5
<211> LENGTH: 101
<212> TYPE: DNA
<213> ORGANISM: Solanum tomato

<400> SEQUENCE: 5
agtcttcctg ctcctggccc ttccgaaaga agtcaacaca gtacttctct tcctcctccc    60
catcagaaag ctcacccctc accagcttat catataactt a                        101

<210> SEQ ID NO 6
<211> LENGTH: 101
<212> TYPE: DNA
<213> ORGANISM: Solanum tomato

<400> SEQUENCE: 6
```

```
gaagatttgt gggtattgat gcaaaagaag aatgttgatg ctgacttggg aagttacacc        60
attagattac aaggattggt tgcgaataac caggttaacg a                          101
```

<210> SEQ ID NO 7
<211> LENGTH: 20
<212> TYPE: DNA
<213> ORGANISM: Artificial sequence
<220> FEATURE:
<223> OTHER INFORMATION: Probe

<400> SEQUENCE: 7

```
cagtacttct cttcctcctc                                                   20
```

<210> SEQ ID NO 8
<211> LENGTH: 22
<212> TYPE: DNA
<213> ORGANISM: Artificial sequence
<220> FEATURE:
<223> OTHER INFORMATION: Probe

<400> SEQUENCE: 8

```
tctaatggtg taacttccca ag                                                22
```

<210> SEQ ID NO 9
<211> LENGTH: 19
<212> TYPE: DNA
<213> ORGANISM: Artificial sequence
<220> FEATURE:
<223> OTHER INFORMATION: Probe

<400> SEQUENCE: 9

```
agtacttctc tccctcctc                                                    19
```

<210> SEQ ID NO 10
<211> LENGTH: 21
<212> TYPE: DNA
<213> ORGANISM: Artificial sequence
<220> FEATURE:
<223> OTHER INFORMATION: Probe

<400> SEQUENCE: 10

```
ctaatggtgt aactccccaa g                                                 21
```

<210> SEQ ID NO 11
<211> LENGTH: 19
<212> TYPE: DNA
<213> ORGANISM: Artificial sequence
<220> FEATURE:
<223> OTHER INFORMATION: Primer

<400> SEQUENCE: 11

```
cctggccctt ccgaaagaa                                                    19
```

<210> SEQ ID NO 12
<211> LENGTH: 27
<212> TYPE: DNA
<213> ORGANISM: Artificial sequence
<220> FEATURE:
<223> OTHER INFORMATION: Primer

<400> SEQUENCE: 12

```
gtgggtattg atgcaaaaga agaatgt                                           27
```

<210> SEQ ID NO 13
<211> LENGTH: 19

```
<212> TYPE: DNA
<213> ORGANISM: Artificial sequence
<220> FEATURE:
<223> OTHER INFORMATION: Primer

<400> SEQUENCE: 13
gggtgagctt tctgatggg                                              19

<210> SEQ ID NO 14
<211> LENGTH: 24
<212> TYPE: DNA
<213> ORGANISM: Artificial sequence
<220> FEATURE:
<223> OTHER INFORMATION: Primer

<400> SEQUENCE: 14
tcgttaacct ggttattcgc aacc                                        24

<210> SEQ ID NO 15
<211> LENGTH: 15
<212> TYPE: DNA
<213> ORGANISM: Lycopersicon esculentum

<400> SEQUENCE: 15
ctcaatggca aacaa                                                  15

<210> SEQ ID NO 16
<211> LENGTH: 16
<212> TYPE: DNA
<213> ORGANISM: Lycopersicon esculentum

<400> SEQUENCE: 16
cctcaatgac aaacaa                                                 16

<210> SEQ ID NO 17
<211> LENGTH: 24
<212> TYPE: DNA
<213> ORGANISM: Lycopersicon esculentum

<400> SEQUENCE: 17
agaaaaatgt ggccatgggt aact                                        24

<210> SEQ ID NO 18
<211> LENGTH: 25
<212> TYPE: DNA
<213> ORGANISM: Lycopersicon esculentum

<400> SEQUENCE: 18
ggtagcctta gatgcaatag tgtga                                       25

<210> SEQ ID NO 19
<211> LENGTH: 17
<212> TYPE: DNA
<213> ORGANISM: Lycopersicon esculentum

<400> SEQUENCE: 19
tctacacaaa agaatgc                                                17

<210> SEQ ID NO 20
<211> LENGTH: 17
<212> TYPE: DNA
<213> ORGANISM: Lycopersicon esculentum

<400> SEQUENCE: 20
```

```
tctacacaaa cgaatgc                                                  17

<210> SEQ ID NO 21
<211> LENGTH: 24
<212> TYPE: DNA
<213> ORGANISM: Lycopersicon esculentum

<400> SEQUENCE: 21
cttgggagat actctctgtt gctt                                          24

<210> SEQ ID NO 22
<211> LENGTH: 26
<212> TYPE: DNA
<213> ORGANISM: Lycopersicon esculentum

<400> SEQUENCE: 22
gcccaacaga tgatctttaa gaatgg                                        26
```

TOMATO PLANTS WITH IMPROVED DISEASE RESISTANCE

CROSS REFERENCE TO RELATED APPLICATIONS

This application is a divisional of U.S. Ser. No. 14/882,384, filed Oct. 13, 2015, which claims priority to U.S. Provisional Application No. 62/064,375, filed Oct. 15, 2014, the disclosures of which are herein incorporated by reference in their entireties.

FIELD OF THE INVENTION

The present invention relates to the field of agriculture and more specifically to methods and compositions for producing tomato plants exhibiting disease resistance with reduced plant necrosis.

INCORPORATION OF SEQUENCE LISTING

The sequence listing that is contained in the file named "SEMB019US_ST25," which is 11.1 kilobytes as measured in Microsoft Windows operating system and was created on Oct. 13, 2015, is filed electronically herewith and incorporated herein by reference.

BACKGROUND OF THE INVENTION

Disease resistance is an important trait in agriculture, particularly for the production of food crops. Although disease resistance alleles have been identified in uncultivated tomato lines, efforts to introduce these alleles into cultivated lines are hindered by the introduction of deleterious traits together with the resistance alleles. The use of marker-assisted selection (MAS) in plant breeding methods has made it possible to select plants based on genetic markers linked to traits of interest. However, accurate markers for identifying or tracking desirable traits in plants are frequently unavailable even if a gene associated with the trait has been characterized. These difficulties are further complicated by factors such as polygenic or quantitative inheritance, and an often incomplete understanding of the genetic background underlying expression of a desired phenotype. Therefore, in the absence of accurate and validated markers for use in MAS, it may not be feasible to produce new plant lines exhibiting certain disease resistant phenotypes.

SUMMARY OF THE INVENTION

In one aspect, the invention provides a tomato plant of a cultivated tomato plant variety comprising a recombinant introgression from *Solanum chilense* on chromosome 6, wherein said recombinant introgression comprises a first allele conferring improved resistance to tomato yellow leaf curl virus relative to a plant lacking said first allele, and wherein said recombinant introgression lacks a second allele genetically linked to said first allele and conferring necrosis. In certain embodiments, the recombinant introgression from *Solanum chilense* is located between approximately 30.20 Mbp and 30.88 Mbp on chromosome 6, or is located between approximately 30.69 Mbp and 30.88 Mbp on chromosome 6, or is located between approximately 30.71 Mbp and 30.88 Mbp on chromosome 6, or is located between approximately 30.32 Mbp and 30.71 Mbp on chromosome 6, or is located between approximately 30.88 Mbp and 31.80 Mbp on chromosome 6.

In other embodiments, the plant comprises a *Solanum chilense* allele at locus NSLYC008383071 (SEQ ID NO:1) and lacks a *Solanum chilense* allele at locus NSLYC005134429 (SEQ ID NO:3) or the plant comprises a *Solanum chilense* allele at locus NSLYC008383071 (SEQ ID NO:1) and lacks a *Solanum chilense* allele at locus NSLYC009077970 (SEQ ID NO:2), or the plant comprises *S. chilense* donor DNA within a genomic segment flanked by NSLYC005134429 (SEQ ID NO:3) and NSLYC008383071 (SEQ ID NO:1), or the plant comprises *S. chilense* donor DNA within a genomic segment flanked by NSLYC009077970 (SEQ ID NO:2) and NSLYC008383071 (SEQ ID NO:1), or the plant comprises *S. chilense* donor DNA within a genomic segment flanked by NSLYC008382908 and NSLYC008383071 (SEQ ID NO:1), or the plant comprises *S. chilense* donor DNA within a genomic segment flanked by NSLYC009418370 (SEQ ID NO:4) and NL231193. In another embodiment, the invention provides a plant part of such a plant, including a cell, a seed, a root, a stem, a leaf, a fruit, a flower, or pollen.

In another aspect, the invention provides a method for producing a tomato plant with improved resistance to tomato yellow leaf curl virus comprising: a) crossing the tomato plant of claim 1 with itself or with a second tomato plant of a different genotype to produce one or more progeny plants; and b) selecting a progeny plant comprising said recombinant introgression. In one embodiment, selecting the progeny plant comprises identifying a progeny plant that (1) comprises a *Solanum chilense* allele at a locus genetically linked to said first allele and/or lacks an allele present at the corresponding locus in the tomato plant, and (2) lacks a *Solanum chilense* allele at a locus genetically linked to said second allele that confers necrosis, and/or comprises an allele present at the corresponding locus from in the tomato plant. In another embodiment, selecting said progeny plant comprises marker-assisted selection (MAS). In a further embodiment, marker-assisted selection (MAS) comprises detecting at least one allele at a locus selected from the group consisting of NSLYC005134429 (SEQ ID NO:3), NSLYC009077970 (SEQ ID NO:2), NSLYC009418370 (SEQ ID NO:4), NSLYC008383071 (SEQ ID NO:1), NSLYC008382908, and NL231193. In still further embodiments, the progeny plant is an F2-F6 progeny plant, or producing the progeny plant comprises backcrossing, such as from 2-7 generations of backcrossing.

In another aspect, the invention provides a method for obtaining a tomato plant exhibiting improved resistance to tomato yellow leaf curl virus comprising: a) obtaining a tomato plant heterozygous for a first allele that confers resistance to tomato yellow leaf curl virus and that is genetically linked in the plant to a second allele from *Solanum chilense* that confers necrosis; (b) obtaining progeny of the plant; and (c) selecting at least a first progeny plant in which recombination has occurred such that the progeny comprises said first allele that confers resistance to tomato yellow leaf curl virus but not said second allele that confers necrosis; wherein selecting said first progeny plant comprises detecting at least one allele at a locus selected from the group consisting of NSLYC005134429 (SEQ ID NO:3), NSLYC009077970 (SEQ ID NO:2), NSLYC009418370 (SEQ ID NO:4), NSLYC008383071 (SEQ ID NO:1), NSLYC008382908, and NL231193. In one embodiment, the progeny plant is an F2-F6 progeny plant, or producing the progeny plant comprises backcrossing, such as from 2-7 generations of backcrossing. In another embodiment, the invention provides a plant produced by such a method, or a part of such a plant, selected from the group consisting of a cell, a seed, a root, a stem, a leaf, a fruit, a flower, and pollen.

In another aspect, the invention provides a tomato plant of a cultivated tomato plant variety comprising a TT allele at marker NSLYC008374675 (SEQ ID NO:5), and a GG allele at marker NSLYC008375578 (SEQ ID NO:6), wherein said alleles confer a lack of or resistance to necrosis. In one embodiment, the method further comprises: d) selecting against alleles on chromosome 2 associated with necrosis; wherein said selecting against comprises selecting against plants comprising a CC allele at marker NSLYC008374675 (SEQ ID NO:5), or an AA allele at marker NSLYC008375578 (SEQ ID NO:6), wherein the presence of said alleles confers necrosis.

In another aspect, the invention provides a method for obtaining a tomato plant exhibiting resistance to necrosis comprising: a) obtaining a tomato plant heterozygous for a first allele that confers resistance to necrosis; (b) obtaining progeny of the plant; and (c) selecting at least a first progeny plant in which recombination has occurred such that the progeny comprises said first allele that confers resistance to necrosis; wherein selecting said first progeny plant comprises detecting at least one allele at a locus selected from the group consisting of marker NSLYC008374675 (SEQ ID NO:5) and marker NSLYC008375578 (SEQ ID NO:6), wherein said alleles confer a lack of or resistance to necrosis.

In another aspect, the invention provides a method for obtaining a tomato plant exhibiting improved resistance to tomato yellow leaf curl virus comprising: (a) obtaining a tomato plant heterozygous for a first allele that confers resistance to tomato yellow leaf curl virus and that is genetically linked in the plant to a second allele from *Solanum chilense* that confers necrosis; (b) obtaining progeny of the plant; and (c) selecting at least a first progeny plant in which recombination has occurred such that the progeny comprises said first allele that confers resistance to tomato yellow leaf curl virus but not said second allele that confers necrosis. In accordance with the invention, selecting a progeny plant may comprise selecting a plant that comprises an allele that confers resistance to tomato yellow leaf curl virus from *Solanum chilense* chromosome 6, and lacks a second locus linked thereto conferring one or more of necrosis, reduced fruit set, or reduced fruit size, relative to a plant that lacks the second locus. In one embodiment of the method, selecting said first progeny plant comprises selecting a progeny wherein recombination has occurred between locus NSLYC009418370 (SEQ ID NO:4) and locus NL231193. In a specific embodiment, the method comprises detecting at least one allele at a locus selected from the group consisting of NSLYC008383071 (SEQ ID NO:1), NSLYC009418370 (SEQ ID NO:4), NSLYC008382908, and NL231193. In another embodiment, the method comprises (d) selecting a further progeny plant from among the plants selected in step (c); wherein selecting said further progeny plant comprises detecting at least one allele at a locus selected from the group consisting of NSLYC009418370 (SEQ ID NO:4) and NL231193. In yet another embodiment, the invention provides a plant produced by any of the foregoing methods.

BRIEF DESCRIPTION OF THE DRAWINGS

FIG. 1: Shows a comparison of recombinants in the Mi (nematode)—Ty (geminivirus) region of chromosome 6. Columns from left to right are: genetic sources, 22 marker assays including marker for the nematode trait (1), and three Ty-1 markers for the geminivirus trait (2-4), followed by phenotyping results from geminivirus agroinoculation, field resistance, and an assessment of leaf necrosis, which is a manifestation of genetic drag from the Ty-1 introgression. Genotypes are indicated by shading as shown in the figure legend. "nd" indicates no data.

FIG. 3: Shows the average necrosis rating for several F3 lines comprising Ty-1 introgressions, together with the genotype at several marker loci. "esc" refers to DNA originating from *S. esculentum* at the given marker locus, and "chi" refers to DNA originating from *S. chilense* at the given marker locus.

FIG. 5: Shows the average necrosis rating for several plant lines, together with genotypes at two marker loci on chromosome 2 associated with necrosis as shown in FIG. 2.

FIG. 6: Shows the genotype of a set of F4 recombinant lines at several marker loci in the approximate region of Ty-1 (between 20 and 34 Mbp of chromosome 6). The highly correlated TaqMan assay based on a SNP is NSLYC008426102. A gray SNP means identical to SNP present in susceptible parents (FIR-16-1078 and FDR-16-0197) and a white SNP means identical to SNP present in resistant parents (FIR-AY06074 and FDR-16-2133). In the second column, the TYLCV test scores are shown.

FIG. 7: Shows the genotype of a set of recombinant lines at several marker loci in the approximate region of Ty-1 (between 30.3 Mbp and 31.8 Mbp of chromosome 6). Gray indicates a donor *S. chilense* allele and white indicates a recipient *S. esculentum* allele.

DETAILED DESCRIPTION

Figure 2:
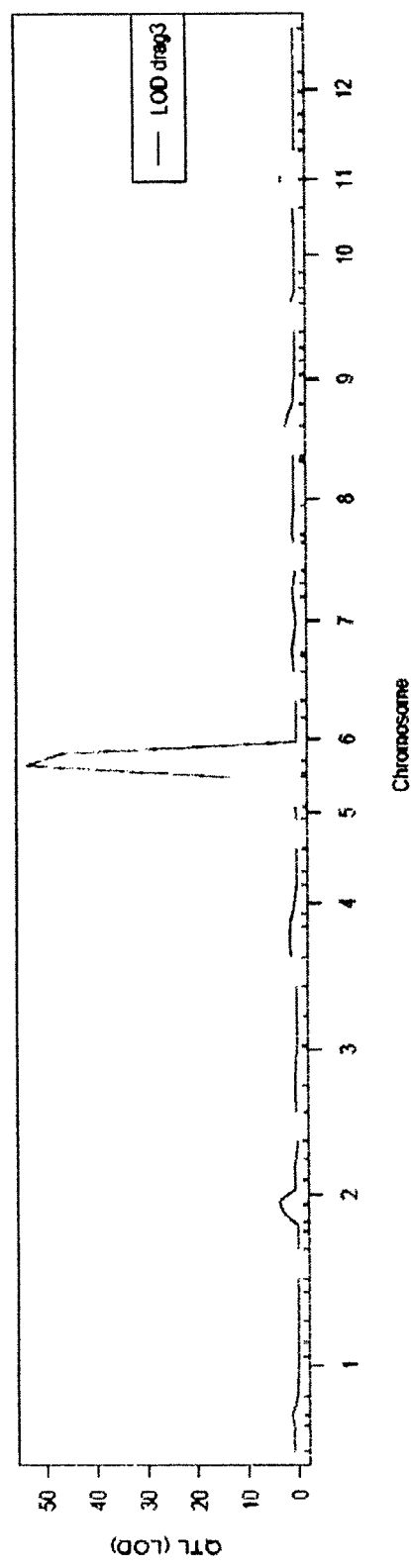
FIG. 2: Shows an LOD plot derived from genotypic and phenotypic data in an F2 population comprising a Ty-1 introgression from *S. chilense*.

Tomato yellow leaf curl virus (TYLCV) is a plant pathogenic virus which is responsible for severe yield loss in tomato plants. Several wild tomato species are known to exhibit resistance to TYLCV, and intensive efforts have been made to introgress TYLCV resistance alleles from these species into cultivated tomato lines. However, these efforts have been hampered because resistance alleles from wild species are accompanied by undesirable agronomic traits such as necrosis. Yield loss due to TYLCV in tomato plants remains a significant problem.

For the first time, the invention provides novel introgressions of disease resistance alleles from *Solanum chilense* into cultivated or elite tomato lines, resulting in tomato plants exhibiting high levels of resistance to TYLCV without the deleterious necrosis previously associated with Ty1 introgressions from wild species. In a specific embodiment, the present invention may be used in the *Lycopersicon esculentum* (aka *Solanum lycopersicum*) species of tomato. The invention therefore represents a significant advance in the art. By further providing novel, accurate markers for tracking the introgressed alleles without associated necrosis during plant breeding, the invention permits introgression of the disease resistance into any desired tomato genotype.

Resistance to TYLCV has conventionally been obtained through introgressions of the Ty-1 locus from *S. chilense*. However, Ty-1 introgressions are typically large, and plants comprising these introgressions exhibit agronomically unacceptable traits including necrosis. Efforts to reduce the incidence or severity of necrosis in plants comprising Ty-1 introgressions have been unsuccessful in part due to suppressed recombination in the centromeric region of chromosome 6 near the Ty-1 locus. In addition, several genetic regions surrounding the Ty-1 locus are inverted in wild tomato lines compared with cultivated lines, further interfering with recombination. Introgression of Ty-1 alleles from *S. chilense* is even further complicated by a lack of existing markers and assays that accurately correlate genotype with resistance and reduced necrosis over a variety of tomato lines.

Despite the many obstacles to the successful introgression of Ty-1 resistance alleles from *S. chilense* into cultivated tomato lines, the present inventors were surprisingly able to produce novel introgressions from *S. chilense* which confer resistance to TYLCV without the deleterious traits previously associated with Ty-1 introgressions. In some embodiments, the invention provides plants comprising donor *S. chilense* DNA at marker NSLYC008383071 (SEQ ID NO:1) and recipient DNA at marker NSLYC009077970 (SEQ ID NO:2). In other embodiments, the invention provides plants comprising donor *S. chilense* DNA at marker NSLYC008383071 (SEQ ID NO:1) and recipient DNA at marker NSLYC005134429 (SEQ ID NO:3). In other embodiments, the invention provides plants comprising *S. chilense* donor DNA within a genomic segment flanked by NSLYC009077970 (SEQ ID NO:2) and NSLYC008383071 (SEQ ID NO:1) or within a genomic segment flanked by NSLYC005134429 (SEQ ID NO:3) and NSLYC008383071 (SEQ ID NO:1).

The present invention further provides novel trait-linked markers which can be used to produce plants comprising novel recombined introgressions in the Ty-1 region of chromosome 6 conferring TYLCV resistance without necrosis. In particular embodiments, the invention provides the markers shown in Tables 1, 4, 6, and 7. Other embodiments of the invention provide novel markers NSLYC008383071 (SEQ ID NO:1), NSLYC009418370 (SEQ ID NO:4), NSLYC009077970 (SEQ ID NO:2), and NSLYC005134429 (SEQ ID NO:3) which have been shown to be genetically linked to TYLCV resistance in plants.

The invention further provides Ty-1 introgressions which can be deployed homozygously without detrimental necrosis or other unacceptable traits. Ty-1 alleles have conventionally been deployed heterozygously in an effort to reduce the severity of the necrotic symptoms exhibited by plants comprising Ty-1 introgressions. However, contrary to the belief in the field that heterozygous deployment of Ty-1 alleles derived from *S. chilense* in an elite line was necessary to avoid negative traits such as necrosis, the present invention provides Ty-1 resistance alleles which can be deployed homozygously without unacceptable levels of necrosis in plants. The novel, reduced introgressions of the present invention therefore provide significant advantages over existing technology.

The invention further identifies a novel QTL conferring resistance to necrosis on tomato chromosome 2, as well as nucleic acid sequences and genetic markers associated with the QTL. The use of the novel markers provided herein for selection of plants having favorable alleles within or genetically linked to this locus allows for the development of plants with reduced or absent necrotic symptoms. In some embodiments, the invention therefore provides methods of producing plants having decreased or absent necrotic symptoms by selecting or breeding plants having favorable alleles at the markers on chromosome 2 disclosed herein. In certain embodiments, the invention provides plants having a TT allele within marker NSLYC008374675 (SEQ ID NO:5) and plants having a GG allele within marker NSLYC008375578 (SEQ ID NO:6) which exhibit decreased necrosis compared with plants not comprising these alleles.

The invention further provides novel markers and assays that allow the accurate identification and tracking of the genomic regions provided herein during plant breeding. Because genetically diverse tomato lines can be difficult to cross due in part to suppressed recombination in the Ty-1 region, the introduction of TYLCV resistance alleles without associated necrosis from *S. chilense* into elite tomato lines or cultivated lines using conventional breeding methods would require prohibitively large segregating populations for progeny screens with an uncertain outcome. Marker-assisted selection (MAS) is therefore an improvement in the effective introgression of wild tomato alleles into elite cultivars. However, previously known markers for TYLCV resistance have not allowed selection of TYLCV resistance without associated necrosis. In contrast, the present invention enables MAS of Ty1 without associated necrosis by providing improved and validated markers for detecting genotypes associated with disease resistance and reduced necrosis without the need to grow large populations of plants to maturity in order to observe the phenotype.

I. Genomic Regions, Alleles, and Polymorphisms Associated with TYLCV Resistance and Reduced Necrosis in Tomato Plants The invention provides novel introgressions of one or more alleles associated with disease resistance and reduced plant necrosis in tomato plants, together with polymorphic nucleic acids and linked markers for tracking the introgressions during plant breeding.

TYLCV can infect tomato plants at any stage in the growth cycle and can cause severe reduction in yield and quality in a tomato crop. Intensive efforts have therefore been made to identify effective sources of TYLCV resistance. However, previously known introgressions from wild species have been associated with plant necrosis. In particular, cultivated tomato lines carrying previously known introgressions of TYLCV resistance genes exhibit necrosis of the leaves. Despite many years of selective breeding in an effort to reduce the incidence of necrosis, these effects are still routinely observed in the field.

Wild tomato types exhibiting TYLCV resistance, for example *S. chilense*, are known in the art and may be used in accordance with certain embodiments of the invention. Other TYLCV resistance sources have also been described and are known in the art (see, for example, Vidaysky et al., *Phytopathology*, 88(9):910-4, 1998; Hutton et al., *HortScience*, 47(3):324-327, 2012; Ji et al., *HortScience*, 44(3): 614-618, 2009).

Using the improved genetic markers and assays of the invention, Applicants were able to successfully identify a novel TYLCV resistance region from *S. chilense* associated with fewer deleterious traits when introgressed into a cultivated line. In certain embodiments, the invention provides plants comprising donor *S. chilense* DNA at marker NSLYC008383071 (SEQ ID NO:1) and recipient DNA at marker NSLYC009077970 (SEQ ID NO:2). In other embodiments, the invention provides plants comprising donor *S. chilense* DNA at marker NSLYC008383071 (SEQ ID NO:1) and recipient DNA at marker NSLYC005134429 (SEQ ID NO:3). In other embodiments, the invention provides plants comprising *S. chilense* donor DNA within a genomic segment flanked by NSLYC009077970 (SEQ ID NO:2) and NSLYC008383071 (SEQ ID NO:1) or a genomic segment flanked by NSLYC005134429 (SEQ ID NO:3) and NSLYC008383071 (SEQ ID NO:1).

The invention further identifies and provides genomic segments from approximately 30.20 Mbp (NSLYC005134429, SEQ ID NO:3) to 30.88 Mbp (NSLYC009418370, SEQ ID NO:4), from approximately 30.69 Mbp (NSLYC009077970, SEQ ID NO:2) to 30.88 Mbp (NSLYC009418370, SEQ ID NO:4), or from approximately 30.71 Mbp (NSLYC008383071, SEQ ID NO:1) to 30.88 Mbp (NSLYC009418370, SEQ ID NO:4) on chromosome 6 associated with TYLCV resistance, but not associated with necrosis when introgressed into cultivated tomato lines. In particular embodiments, the invention provides a plant comprising recipient DNA at one or more of markers NL0232061, NL0216350, NL0244835, NSLYC005134413, NSLYC005134429 (SEQ ID NO:3), and NSLYC008382908, and comprising *S. chilense* donor DNA at one or more of markers NSLYC008373232, NSLYC009078368, NSLYC009077969, NSLYC009077970 (SEQ ID NO:2), NSLYC008383071 (SEQ ID NO:1), NSLYC009418370 (SEQ ID NO:4), NSLYC008426177, and NL231193, which exhibits resistance to TYLCV and does not exhibit necrosis.

In another embodiment, the invention provides novel markers that may be used to identify a locus as described herein, such as the markers set forth in Tables 1, 4, 6, and 7. Other embodiments of the invention provide novel markers NSLYC008383071 (SEQ ID NO:1), NSLYC009418370 (SEQ ID NO:4), NSLYC009077970 (SEQ ID NO:2), and NSLYC005134429 (SEQ ID NO:3) which have been shown to be genetically linked to TYLCV resistance in plants.

II. Introgression of Genomic Regions Associated with Disease Resistance

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel accurate markers for identifying and tracking introgression of one or more of the genomic regions from *S. chilense* disclosed herein into cultivated lines. The invention further provides markers for identifying and tracking the novel introgressions disclosed herein during plant breeding, including markers set forth in Tables 1, 4, 6, and 7. Other embodiments of the invention provide novel markers NSLYC008383071 (SEQ ID NO:1), NSLYC009418370 (SEQ ID NO:4), NSLYC009077970 (SEQ ID NO:2), and NSLYC005134429 (SEQ ID NO:3) which have been shown to be genetically linked to TYLCV resistance in plants.

Markers within or linked to any of the genomic intervals of the present invention may be useful in a variety of breeding efforts that include introgression of genomic regions associated with disease resistance into a desired genetic background. For example, a marker within 40 cM, 20 cM, 15 cM, 10 cM, 5 cM, 2 cM, or 1 cM of a marker associated with disease resistance described herein can be used for marker-assisted introgression of genomic regions associated with a disease tolerant phenotype.

Tomato plants comprising one or more introgressed regions associated with a desired phenotype wherein at least 10%, 25%, 50%, 75%, 90%, or 99% of the remaining genomic sequences carrying markers characteristic of the germplasm are also provided. Tomato plants comprising an introgressed region comprising regions closely linked to or adjacent to the genomic regions and markers provided herein and associated with a disease resistance phenotype are also provided.

III. Development of Disease Resistant Tomato Varieties

For most breeding objectives, commercial breeders work within germplasm that is "cultivated," "cultivated type" or "elite." "Elite" varieties refer to varieties that have resulted from breeding and selection for superior agronomic performance, including yield and other selected traits. Similarly, "cultivated" varieties or "cultivars" are plants or groups of plants selected for desirable characteristics for cultivation in agriculture and that can be maintained through propagation of the variety. Elite varieties or cultivars are easier to breed because they generally perform well when evaluated for horticultural performance. A number of cultivated and elite tomato (*S. lycopersicum* or *L. esculentum*) types have been developed, which are agronomically superior and appropriate for commercial cultivation. However, the performance advantage a cultivated germplasm provides can be offset by a lack of allelic diversity. Breeders generally accept this tradeoff because progress is faster when working with cultivated material than when breeding with genetically diverse sources. Thus, in certain embodiments, the present invention provides novel introgressions of disease resistance alleles from *Solanum chilense* into an elite tomato line, or into a cultivated tomato line, resulting in tomato plants exhibiting high levels of resistance to TYLCV without the deleterious necrosis previously associated with Ty1 introgressions from wild species. Such introgressions may provide superior tomato plants that may possess a number of agronomically elite traits, in addition to the novel introgression of the present invention.

In contrast, when cultivated germplasm is crossed with non-cultivated germplasm, a breeder can gain access to novel alleles from the non-cultivated type. However, this approach presents significant difficulties due to fertility problems associated with crosses between diverse lines, and negative linkage drag from the non-cultivated parent. In tomato plants, non-cultivated types such as *S. chilense* can provide alleles associated with disease resistance. However, these non-cultivated types may have poor horticultural qualities such as vulnerability to necrosis or fruit defects.

The process of introgressing desirable resistance genes from non-cultivated lines into elite cultivated lines while avoiding problems with linkage drag or low heritability is a long and often arduous process. Success in deploying alleles derived from wild relatives therefore strongly depends on minimal or truncated introgressions that lack detrimental effects and reliable marker assays that replace phenotypic screens. Success is further defined by simplifying genetics for key attributes to allow focus on genetic gain for quantitative traits such as disease resistance. Moreover, the process of introgressing genomic regions from non-cultivated lines can be greatly facilitated by the availability of accurate markers for MAS.

One of skill in the art would therefore understand that the alleles, polymorphisms, and markers provided by the invention allow the tracking and introduction of any of the genomic regions identified herein into any genetic background. In addition, the genomic regions associated with disease resistance disclosed herein can be introgressed from one genotype to another and tracked using MAS. Thus, Applicants' discovery of accurate markers associated with disease resistance will facilitate the development of tomato plants having beneficial phenotypes. For example, seed can be genotyped using the markers of the present invention in order to select for plants comprising desired genomic regions associated with disease resistance. Moreover, MAS allows identification of plants homozygous or heterozygous for a desired introgression.

Inter-species crosses can also result in suppressed recombination and plants with low fertility or fecundity. For example, suppressed recombination has been observed for the tomato nematode resistance gene Mi, the Mla and Mlg genes in barley, the Yr17 and Lr20 genes in wheat, the Run1 gene in grapevine, and the Rma gene in peanut. Meiotic recombination is essential for classical breeding because it enables the transfer of favorable alleles across genetic backgrounds, the removal of deleterious genomic fragments, and pyramiding of traits that are genetically linked. Therefore, in the absence of accurate markers, suppressed recombination forces breeders to enlarge segregating populations for progeny screens.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among tomato species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

IV. Molecular Assisted Breeding Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Marker discovery and development in crop plants provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita et al. (1989) Genomics, 8(2), 271-278), denaturing gradient gel electrophoresis (Myers (1985) EPO 0273085), or cleavage fragment length polymorphisms (Life Technologies, Inc., Gathersberg, Md.), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al. (1992) Biotechniques 12(1), 82-87), or PCR amplification of multiple specific alleles (PAMSA; Dutton and Sommer (1991) Biotechniques, 11(6), 700-7002).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a tomato plant a genotype associated with disease resistance, identify a tomato plant with a genotype associated with disease resistance, and to select a tomato plant with a genotype associated with disease resistance. In certain embodiments of methods of the invention, polymorphic nucleic acids can be used to produce a tomato plant that comprises in its genome an introgressed locus associated with disease resistance. In certain embodiments of the invention, polymorphic nucleic acids can be used to breed progeny tomato plants comprising a locus associated with disease resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease resistance in tomato plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201,184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613; 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523 (2003); Cui et al., *Bioinformatics* 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe has a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle, DNA polymerase with 5' 3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which tomato plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, an "elite" variety means any variety that has resulted from breeding and selection for superior agronomic performance including yield and other selected traits. An "elite plant" refers to a plant belonging to an elite variety and which possesses various desirable traits. Numerous elite varieties are available and known to those of skill in the art of tomato breeding. An "elite population" is an assortment of elite individuals or varieties that can be used to represent the state of the art in terms of agronomically superior genotypes of a given crop species, such as tomato. Similarly, an "elite germplasm" or elite strain of germplasm is an agronomically superior germplasm.

A "cultivated" variety or "cultivar" is a plant or group of plants selected for desirable characteristics when grown in agriculture that can be maintained through propagation of the variety. A cultivated variety is not naturally occurring in the wild, and is instead the result of human intervention to obtain desirable characteristics for cultivation.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the term "linked," when used in the context of nucleic acid markers and/or genomic regions, means that the markers and/or genomic regions are located on the same linkage group or chromosome such that they tend to segregate together at meiosis.

As used herein, the term "necrosis," when used in the context of a plant or plant tissue, refers to tissue that turns brown and dies. As used herein, "necrosis" may also include the incidence of chlorosis, where chlorotic tissue is marked by the yellow or white discoloration of normally green tissue.

As used herein, "resistance locus" means a locus associated with resistance or tolerance to disease. For instance, a resistance locus according to the present invention may, in one embodiment, control resistance or susceptibility for tomato yellow leaf curl virus (TYLCV).

As used herein, "resistance allele" means the nucleic acid sequence associated with resistance or tolerance to disease.

As used herein "resistance" or "improved resistance" in a plant to disease conditions is an indication that the plant is more able to reduce disease burden than a non-resistant or less resistant plant. Resistance is a relative term, indicating that a "resistant" plant is more able to reduce disease burden compared to a different (less resistant) plant (e.g., a different plant variety) grown in similar disease conditions. One of skill will appreciate that plant resistance to disease conditions varies widely, and can represent a spectrum of more-resistant or less-resistant phenotypes. However, by simple observation, one of skill can generally determine the relative resistance of different plants, plant varieties, or plant families under disease conditions, and furthermore, will also recognize the phenotypic gradations of "resistant."

One of skill will appreciate that plant resistance to disease conditions varies widely, and can represent a spectrum of more-resistant or less-resistant phenotypes. However, by simple observation, one of skill can generally determine the relative resistance or susceptibility of different plants, plant lines or plant families under disease conditions, and furthermore, will also recognize the phenotypic gradations of "resistant."

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

EXAMPLES

Example 1

Identification of Recombinant Tomato Lines Comprising Ty-1

The Ty-1 TYLCV resistance locus from *S. chilense* LA1969 was introgressed into elite *S. lycopersicon* plants, resulting in several breeding lines with a high level of resistance to TYLCV. However, these lines exhibited undesirable agronomic traits associated with the Ty-1 introgression from *S. chilense*, including necrosis. The molecular markers shown in Table 1 were developed for identification of recombinants maintaining TYLCV resistance with reduced incidence of necrosis.

TABLE 1

Markers on chromosome 6 for identification of Ty-1 recombinants.

| Marker | Position |
| --- | --- |
| NL0233580 | 24,527,065 |
| NL0233570 | 3,293,791 |
| NL0234045 | 22,036,414 |
| NL0233833 | 34,148,452 |
| NL0233541 | 3,294,160 |
| NL0347537 | 28,852,768 |
| NL0347530 | 3,329,633 |
| NL0347552 | 23,690,907 |
| NL0244835 | 29,785,303 |
| NL0231187 | 31,166,320 |
| NL5113529 | 27,693,113 |
| NL5113524 | 2,404,524 |
| NL5113488 | 2,207,760 |
| NL5113492 | 634,983 |
| NL5113500 | 2,842,081 |
| NL5113496 | 3,540,443 |
| NL5113520 | 30,622,375 |
| NL5113518 | 1,162,062 |
| NL5113489 | 1,238,761 |
| NL5113515 | 21,357,322 |
| NL5113464 | 31,664,916 |
| NL5132888 | 20,421,231 |
| NL0215181 | 14,499,315 |
| NL0216011 | 23,120,245 |
| NL0217856 | 12,044,896 |
| NL0216387 | 22,496,662 |
| NL5132908 | 20,493,538 |
| NL5132893 | 3,020,831 |
| NL5132900 | 20,710,909 |
| NL5132906 | 8,115,068 |

The use of these Ty-1 linked markers led to the identification of tomato lines 11039-1, 09GA0361-11 and 08TK01-26-2. As shown in FIG. 1, Line 11039-1 comprises a recombination between markers Q_NL5113515 and Q_NL5113488. This line is TYLCV susceptible but still exhibits leaf necrosis, suggesting that the Ty-1 resistance locus is positioned to the right (south on the chromosome) of marker Q_NL5113515, while at least some component of the necrosis locus from the *S. chilense* introgression is located to the left (north on the chromosome) of marker Q_NL5113488. Line 09GA0361-11 comprises a recombination to the right of CD67 and is TYLCV resistant, while exhibiting reduced leaf necrosis. An even smaller introgression was identified in line 08TK01-26-2, which exhibits TYLCV resistance in the field and under more controlled conditions (agro-inoculation with TYLCV).

Example 2

Mapping Populations

Parent varieties Petit (FIR-191-PETIT) and Screen (FIR-191-SCREEN) were crossed to create an F2 population for further analysis of necrosis and other traits in plants comprising Ty-1 introgressions. FIR-191-PETIT is the parent comprising the *chilense* introgression. Ninety-two hundred seeds from the F2 population were sown and analyzed with markers NL0232070 and NL0231193 resulting in 209 validated recombinants. Of these recombinants, 42 were grown in the greenhouse to produce selfed (F3) seed, and F3 plants were phenotyped for necrosis. Twenty-five of the F3 lines fixed for a recombination event between NL0232070 and NL0231193 were grown in greenhouse conditions for analysis of the Ty-1 introgression.

Example 3

Evaluation of TYLCV Resistance and Necrosis in Mapping Populations

Plants were evaluated for TYLCV resistance using the following whitefly inoculation protocol. Plants were exposed to whiteflies (*Bemisia tabaci* (Q biotype)) carrying TYLCV for 48 hours at the first true leaf stage (approximately 3 weeks after sowing). Plants were scored for TYLCV resistance according to the scale shown in Table 2 and evaluated for necrosis using the scale shown in Table 3. Scoring was performed 15 and 30 days post inoculation when at least 90% of the susceptible control plants were infected with TYLCV (score 9).

TABLE 2

TYLCV Scoring Scale

| | |
|---|---|
| Rating scale definition | 1 = no symptoms. |
| | 3 = some yellow spots or stripes at the edges of top leaves. |
| | 5 = obvious yellowing of top leaves, no curling. |
| | 7 = obvious yellowing and curling of top leaves. Some growth reduction of plant might occur. |
| | 9 = heavy growth reduction of plant, heavy curling and yellowing of top leaves. |
| Norm to validate bioassay | At least 90% of the susceptible control plants should be infected with TYLCV (score 9). |

TABLE 3

Necrosis Scoring Scale. All leaves are left on the plant for scoring.

| | |
|---|---|
| Rating scale definition | 1 = no necrosis; green leaf. |
| | 2 = leaf edge showing necrosis; remaining leaf is still green. |
| | 3 = light necrosis; some clear necrotic spots on bottom leaves. No chlorosis. Green leaf. |
| | 4 = light necrosis; light spots on the leaf and clear necrotic spots on leaf of bottom part of the plant. |
| | 5 = moderate necrosis; clear spots on leaf and clear necrotic spots on leaf of bottom part of the plant. |
| | 6 = necrosis and light chlorosis on leaf of bottom part of the plant. |

TABLE 3-continued

Necrosis Scoring Scale. All leaves are left on the plant for scoring.

| | |
|---|---|
| | 7 = many necrotic spots and chlorosis on leaf of about 75% of the plant. |
| | 8 = severe necrosis and chlorosis. Only top of the plant has some green leaves left. |
| | 9 = plant completely necrotic and chlorotic. |

Example 4

Identification of Necrosis QTL

Seed of the F2 population described in Example 2 was sown and the plants were grown under greenhouse conditions in winter without artificial lighting. Days were <12 h, night temperature was >15° C., and day temperature was a maximum of <25° C. Necrosis was evaluated using the protocol described in Example 3. F2 plants were sampled individually and genotyped with a set of TaqMan assays of markers distributed across the genome. Assay conditions were as follows: 20 sec at 95° C., followed by 35 repeats of 3 sec at 95° C. and 20 seconds at 60° C., and holding at 20° C.

Combining the genotypic and phenotypic data, two QTL with logarithm of the odds (LOD) values >3.0 could be detected using R/qtl with the default settings. The major QTL was located on chromosome 6, as shown in FIG. 2. Table 4 shows the LOD values for the markers flanking the identified QTL on chromosomes 2 and 6.

TABLE 4

LOD data for markers showing significance for necrosis.

| Marker | Chr. | Pos. | LOD |
|---|---|---|---|
| NSLYC008374675 (SEQ ID NO: 5) | 2 | 39 | 3.051654449 |
| NSLYC008375578 (SEQ ID NO: 6) | 2 | 59.57 | 2.589825655 |
| NL0250996 | 6 | 3.3 | 57.03813316 |
| NSLYC009418370 (SEQ ID NO: 4) | 6 | 6.94 | 49.53995957 |
| NSLYC008427230 | 6 | 17.31 | 36.44859245 |

Example 5

Mapping of Necrosis Loci within the Ty-1 Introgression on Chromosome 6

The F3 populations described in Example 2 comprising *S. chilense* Ty-1 introgressions were further analyzed to identify loci associated with necrosis derived from Ty-1 introgressions. Table 5 shows necrosis scoring results for F3 populations, as well as average necrosis scores for each line at April and May time points. A set of markers was developed to genotype these F3 populations in the region surrounding Ty-1, and these markers are shown in Table 6.

When analyzing the Ty-1 region with these markers, it was noted that almost no recombination was observed in the centromeric region of chromosome 6, where Ty-1 is located. The development of additional markers in the 5-25 cM region of chromosome 6 increased the possibility for detecting recombination events. These novel molecular markers also made it possible to screen large populations to select plants comprising smaller Ty-1 introgressions which exhibited high levels of resistance to TYLCV conferred by the Ty-1 resistance gene, while also reducing or eliminating the occurrence of undesirable agronomic traits previously associated with Ty-1 introgressions, such as necrosis.

Figure 4:
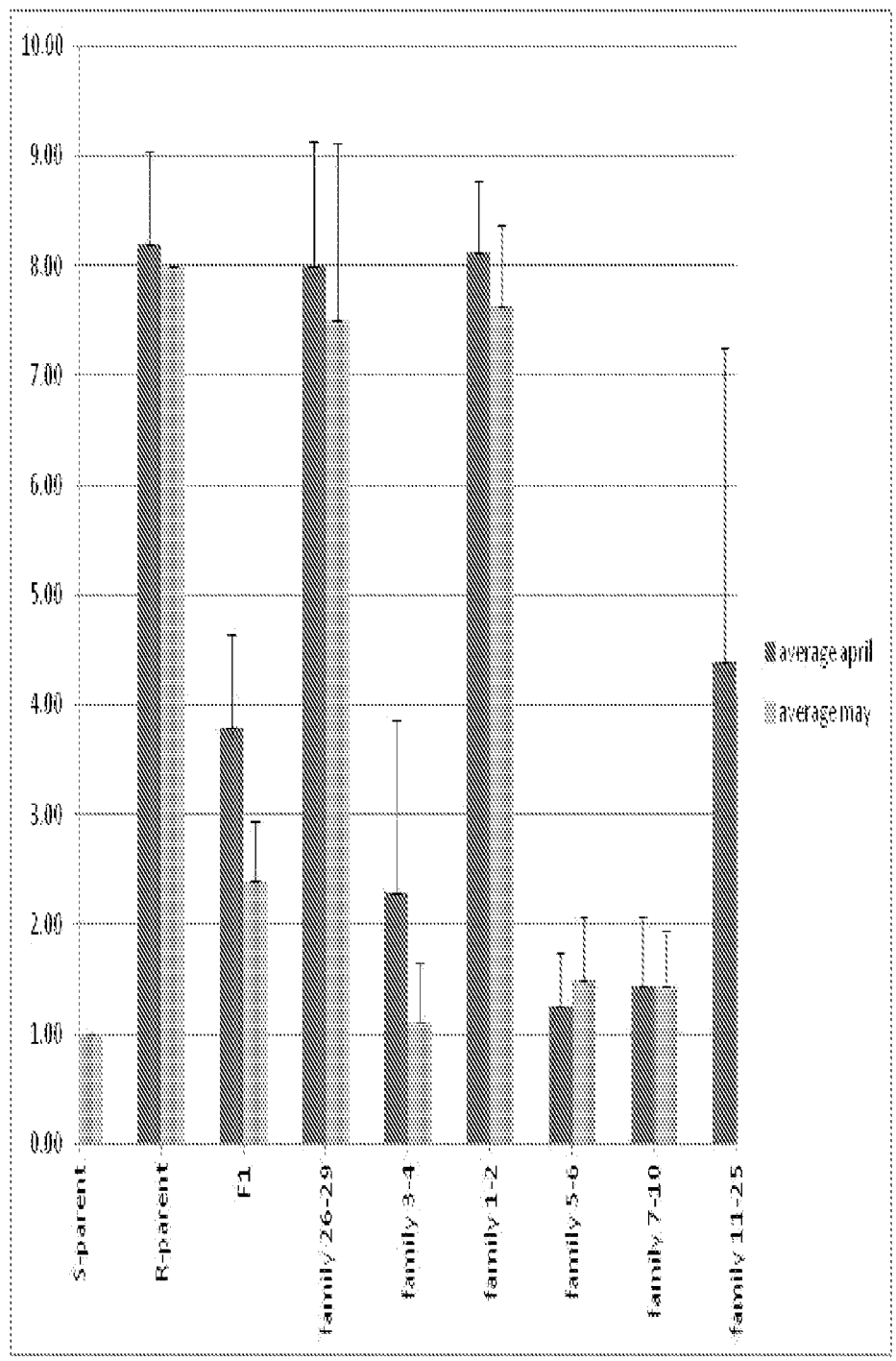
FIG. 4: Shows the average necrosis score for several of the plant lines shown in FIG. 3 based on the location of the break point between donor *S. chilense* DNA and *S. esculentum* DNA determined using the markers shown in FIG. 3.

FIG. 3 shows genotyping data for control lines and F3 lines comprising recombination events between markers NL0232061 and NL231193. Average necrosis scores at the April and May time points are also shown. FIG. 4 shows the average necrosis score for several of the plant lines shown in FIG. 3 based on the location of the break point between donor *S. chilense* DNA and *S. esculentum* DNA determined using the markers shown in FIG. 3. These data clearly demonstrate that plants comprising a Ty-1 introgression wherein *S. chilense* Ty-1 donor DNA is replaced by *S. esculentum* DNA from the top of the chromosome until marker NSLYC008382908 do not exhibit the increased levels of necrosis previously observed for plants with Ty-1 introgressions.

TABLE 5

Necrosis scoring results for F3 plants.

| F3 Pop. No. | April | | | | Avg | May | | | | Avg |
|---|---|---|---|---|---|---|---|---|---|---|
| | Plant 1 | Plant 2 | Plant 3 | Plant 4 | Apr | Plant 1 | Plant 2 | Plant 3 | Plant 4 | May |
| TJD0015 | 8 | 9 | 8 | 8 | 8 | 7 | 7 | 8 | 7 | 7.25 |
| TJD0006 | 8 | 9 | 7 | 8 | 8 | 8 | 9 | 7 | 8 | 8 |
| TJD0006[1] | 2 | 2 | 1 | 3 | 2 | 1 | 2 | 1 | 2 | 1.5 |
| TJD0013[2] | 3 | 1 | 4 | x | 2.67 | 2 | 1 | 2 | x | 1.67 |
| TJD0021 | 1 | 1 | 2 | x | 2.25 | 1 | 2 | 2 | x | 2.25 |
| TJD0026 | 1 | x | x | x | 1 | 1 | x | x | x | 1 |
| TJD0018 | 1 | 1 | 2 | 1 | 1.25 | 2 | 1 | 2 | 1 | 1.5 |
| TJD0027 | 2 | 2 | 3 | x | 2.33 | 1 | 1 | 2 | x | 1.33 |
| TJD0029 | 1 | 1 | x | x | 1 | 2 | 2 | x | x | 2 |
| TJD0020 | 1 | 1 | 1 | x | 1 | 1 | 1 | 1 | x | 1 |
| TJD0017 | 2 | 2 | 1 | 1 | 1.5 | 1 | 1 | 1 | 1 | 1 |
| TJD0007 | 6 | 5 | 2 | | 4.33 | 5 | 4 | 2 | | 3.67 |
| TJD0022 | 8 | 8 | 9 | 8 | 8.25 | 7 | 7 | 9 | 7 | 7.5 |
| TJD0014[3] | 7 | 1 | x | x | 4 | 4 | 1 | x | x | 2.5 |
| 0014[4] | 7 | 8 | 5 | x | 6.67 | 6 | 7 | 3 | x | 5.33 |
| 0020[4] | 8 | 9 | 8 | 9 | 8.67 | 8 | 8 | 8 | 8 | 8 |
| 0021[4] | 8 | 8 | 8 | 9 | 8.25 | 8 | 8 | 8 | 9 | 8.25 |
| TJD0028 | 3 | 9 | 8 | 9 | 7.25 | 2 | 8 | 7 | 9 | 6.5 |
| TJD0030 | 5 | 2 | 2 | x | 4.25 | 6 | 3 | 2 | x | 4.75 |
| TJD0023 | 5 | 2 | x | x | 3.5 | 6 | 2 | x | x | 4 |
| TJD0002 | 2 | 5 | 2 | x | 3 | 2 | 4 | 3 | x | 3 |
| TJD0004 | 2 | 6 | 7 | 1 | 4 | 2 | 5 | 6 | 1 | 3.5 |
| TJD0005 | 2 | 1 | 3 | 2 | 2 | 2 | 2 | 3 | 3 | 2.5 |
| TJD0008 | 3 | 9 | x | x | 6 | 3 | 7 | x | x | 5 |
| TJD0010 | 4 | 3 | 2 | 2 | 2.75 | 4 | 3 | 2 | 2 | 2.75 |
| TJD0009 | 2 | 1 | 2 | 3 | 2 | 2 | 1 | 2 | 1 | 1.5 |
| 0018[4] | 9 | x | x | x | 9 | 9 | x | x | x | 9 |
| TJD0019 | 8 | 8 | 2 | x | 6 | 7 | 7 | 3 | x | 5.67 |

[1]esc control
[2]ESC control
[3]one plant is heterozygous
[4]chi control

TABLE 6

Sequences associated with markers in Ty-1 region on tomato chromosome 6.

| Marker Name | Phys Pos. | Gen. Pos. | SNP |
|---|---|---|---|
| NL0232061 | 21,597,226 | 4.32 | G/A |
| NL0216350 | 27,605,333 | 4.25 | T/C |
| NL0244835 | 29,785,303 | 7.47 | GGTT/* |
| NSLYC005134413 | 30,027,432 | 7.88 | A/T |
| NSLYC005134429 (SEQ ID NO: 3) | 30,199,948 | 8.23 | */C |
| NSLYC008382908 | 30,322,811 | 8.51 | G/A |
| NSLYC008373232 | 30,523,713 | 8.93 | C/T |
| NSLYC009078368 | 30,623,862 | 9.14 | C/A |
| NSLYC009077969 | 30,658,888 | 9.21 | A/G |
| NSLYC009077970 (SEQ ID NO: 2) | 30,689,718 | 9.27 | G/T |

TABLE 6-continued

Sequences associated with markers in Ty-1 region on tomato chromosome 6.

| Marker Name | Phys Pos. | Gen. Pos. | SNP |
|---|---|---|---|
| NSLYC008383071 (SEQ ID NO: 1) | 30,711,829 | 9.31 | T/C |
| NSLYC009418370 (SEQ ID NO: 4) | 30,876,429 | 9.64 | T/* |
| NSLYC008426177 | 30,892,169 | 9.67 | A/T |
| NL0231193 | 31,800,043 | 11.6 | A/C |
| NL0232070 | 2,633,793 | 3.66 | A/C |
| NSLYC005134405 | 29,150,417 | 6.4 | C/G |

Example 6

Identification of QTL Associated with Necrosis on Chromosome 2

As shown in FIG. 2 and Table 4, a QTL associated with necrosis was identified on chromosome 2. The TT_GG haplotype (the TT allele at marker NSLYC008374675 (SEQ ID NO:5), and the GG allele at marker NSLYC008375578 (SEQ ID NO:6) is associated with reduced or absent necrosis as shown in Table 7 and FIG. 5. Necrosis in plants having a TT_GG haplotype is therefore associated with a different necrosis QTL. The CC_AA haplotype (the CC allele at marker NSLYC008374675 (SEQ ID NO:5), and the AA allele at marker NSLYC008375578 (SEQ ID NO:6) is associated with necrosis. Tomato lines having this allele may exhibit necrosis, although typically at intermediate levels (FIG. 5). The VIC probe sequences, FAM probe sequences, and forward and reverse primers for marker NSLYC008374675 and marker NSLYC008375578 are provided as SEQ ID NOs:7-8, 9-10, 11-12, and 13-14, respectively.

TABLE 7

Markers associated with necrosis on tomato chromosome 2.

| Marker Name | SEQ ID No. | Phys Pos. | Non-necrotic allele | Necrosis allele |
|---|---|---|---|---|
| NSLYC008374675 | 5 | 34,929,994 | TT | CC |
| NSLYC008375578 | 6 | 38,823,651 | GG | AA |

Example 7

TaqMan Assay

A TaqMan assay was developed to detect a SNP on chromosome 6 (base position 32,987,053) using marker NSLYC008426102. Genotyping results on a set of F4 recombinant lines with TaqMan assays located in the Ty-1 region between 20 and 34 Mbp of chromosome 6. The TaqMan assay showed 100% correlation on the existing recombinant population (FIG. 6).

Example 8

Trait Introgression of TYLCV Resistance without Necrosis

A tomato line comprising a conventional Ty-1 introgression and exhibiting necrosis is crossed with a tomato line comprising the reduced Ty-1 introgression described herein and exhibiting little or no necrosis. Progeny plants from this cross are backcrossed to produce a BC1 generation. BC1 progeny plants are selected for the S. esculentum allele at marker NSLYC009077970 (SEQ ID NO:2) indicating the presence of the reduced Ty-1 introgression of the invention. BC1 progeny plants or further progeny plants are selected for the presence of the S. chilense allele at marker NSLYC009418370 (SEQ ID NO:4) to follow the Ty-1 introgression. Additionally, the incidence of necrosis may be further modulated by selecting for alleles associated with an absence of necrosis at the described chromosome 2 QTL interval by using markers NSLYC008374675 (SEQ ID NO:5) and NSLYC008375578 (SEQ ID NO:6).

Example 9

Recombinant Tomato Plants with a Smaller Ty-1 Introgression Size

Figure 8:
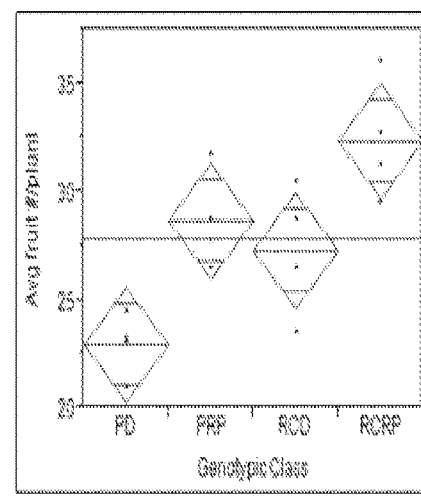
FIG. 8: Shows the results of performance testing for fruit set (total number of mature fruit per number of plants).
Figure 9:
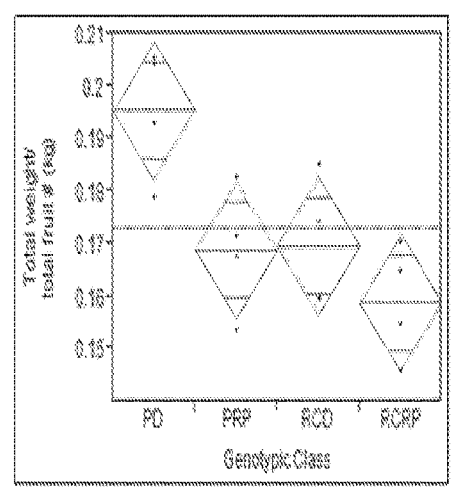
FIG. 9: Shows the results of performance testing for fruit set (total harvest weight in kg per number of fruit).

To create tomato plants with a Ty-1 introgression having less donor S. chilense DNA, initial selection for recombination between markers NSLYC008382908 (8.51 cM) and NSLYC008383071 (9.31 cM, SEQ ID NO:1) was performed in order to break linkage between Ty-1 and undesirable necrosis drag (see FIG. 7). Next, selection for recombination between marker NSLYC009418370 (9.64 cM, SEQ ID NO:4) and NL231193 (11.58 cM) to minimize the amount of S. chilense DNA and thus reduce the size of the introgression. Sequences for markers NSLYC008382908 and NL231193 are provided in Table 9. Select recombinants were tested for resistance to TYLCV by inoculation with whiteflies on 4 replicates of 10 plants each. Additionally, whole plant harvesting of mature fruit and total harvest weight and fruit count were performed on 4 replicates of 6 plants each. The results of the performance testing are shown in Table 8 and FIGS. 8 and 9.

TABLE 8

Mean values for one-way ANOVA of efficacy testing.

| Background | Group A | Group B | Set | DI LSM | Student's t test ($\alpha = 0.05$) |
|---|---|---|---|---|---|
| FDR-14-818 | P | RP | TY1-1 | 9.00 | A |
| FDR-15-2061 | RC | RP | TY1-2 | 9.00 | A |
| FDR-15-2061 | P | RP | TY1-3 | 9.00 | A |
| FDR-15-2061 | P | RP | TY1-4 | 9.00 | A |
| FDR-15-2061 | RC | RP | TY1-4 | 9.00 | A |
| FDR-15-2061 | P | RP | TY1-5 | 8.90 | A |
| FDR-15-2061 | RC | RP | TY1-5 | 8.90 | A |
| FDR-15-2061 | P | RP | TY1-2 | 8.70 | A |
| FDR-14-818 | RC | RP | TY1-1 | 8.40 | A |
| FDR-15-2061 | RC | RP | TY1-3 | 7.48 | B |
| FDR-15-2061 | RC | D | TY1-5 | 4.65 | C |
| FDR-15-2061 | RC | D | TY1-4 | 4.20 | C, D |
| FDR-15-2061 | RC | D | TY1-2 | 4.18 | C, D |
| FDR-9Q08133 | P | D | TY1-1 | 3.80 | D, E |
| FDR-15-2061 | RC | D | TY1-3 | 3.65 | D, E, F |
| FDR-15-2107 | P | D | TY1-5 | 3.25 | E, F |
| FDR-15-2107 | P | D | TY1-4 | 3.04 | E, F |
| FDR-15-2107 | P | D | TY1-3 | 2.97 | F |
| FDR-15-2107 | P | D | TY1-2 | 2.89 | F |
| FDR-14-818 | RC | D | TY1-1 | 2.03 | G |

Figure 10:
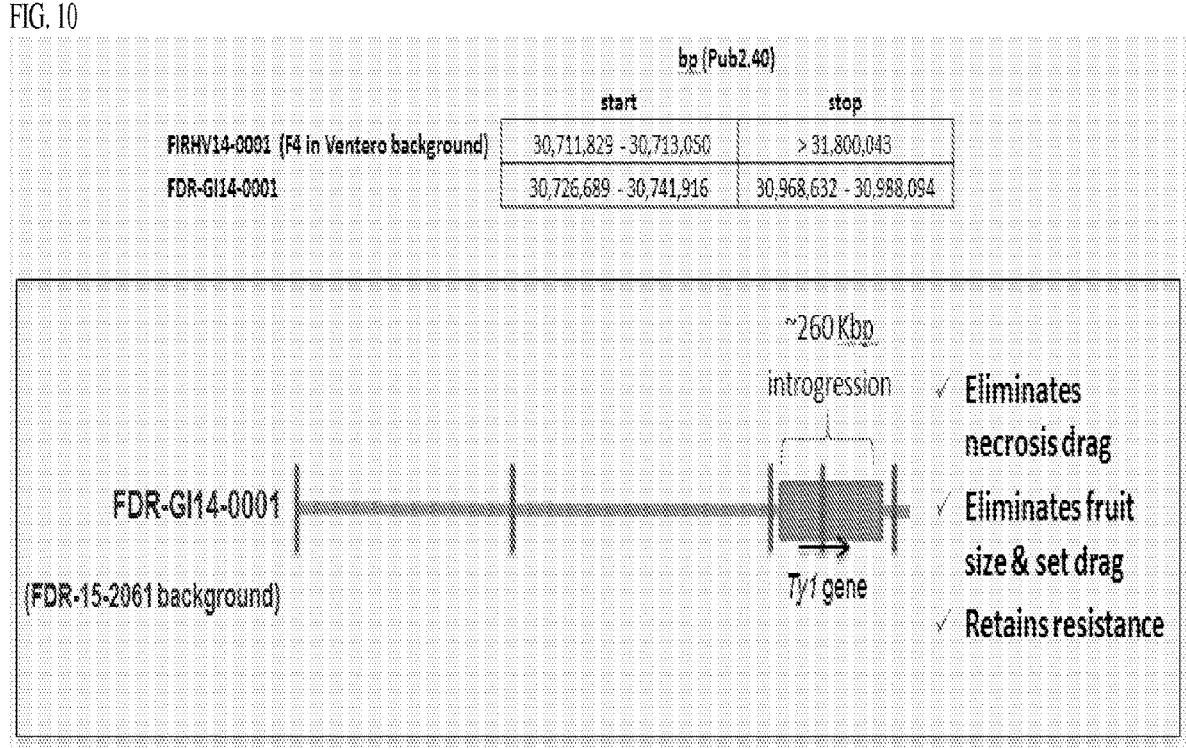
FIG. 10: Shows a depiction of the introgression (approximately 260 kb).

Sequence capture was performed in order to characterize the introgression on tomato chromosome 6 (FIG. 10). The introgression was determined to be approximately 260 kb, and plants into which this introgression was inserted retained resistance to TYLCV while exhibiting a lack of necrosis, and fruit size and fruit set drag.

TABLE 9

Marker Sequences.

| Marker | Alleles | VIC Sequence | FAM Sequence | F Sequence | R Sequence |
|---|---|---|---|---|---|
| NSLYC008382908 | G/A | CTCAATGGCAAACAA (SEQ ID NO: 15) | CCTCAATGACAAACAA (SEQ ID NO: 16) | AGAAAAATGTGGCCATGGGTAACT (SEQ ID NO: 17) | GGTAGCCTTAGATGCAATAGTGTGA (SEQ ID NO:18) |
| NL0231193 | A/C | TCTACACAAAAGAATGC (SEQ ID NO: 19) | TCTACACAAACGAATGC (SEQ ID NO: 20) | CTTGGGAGATACTCTCTGTTGCTT (SEQ ID NO: 21) | GCCCAACAGATGATCTTTAAGAATGG (SEQ ID NO: 22) |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for producing a tomato plant with improved resistance to tomato yellow leaf curl virus, said method comprising:
   (a) crossing a tomato plant of a cultivated tomato plant variety comprising a recombinant introgression from *Solanum chilense* on chromosome 6 with itself or with a second tomato plant of a different genotype to produce one or more progeny plants, wherein said recombinant introgression comprises *Solanum chilense* DNA at locus NSLYC008383071 (SEQ ID NO: 1) conferring improved resistance to tomato yellow leaf curl virus relative to a plant lacking said *Solanum chilense* DNA at locus NSLYC008383071, and wherein said recombinant introgression lacks *Solanum chilense* DNA at locus NSLYC009077970 (SEQ ID NO: 2) genetically linked to said *Solanum chilense* DNA at locus NSLYC008383071 that confers necrosis when present; and
   (b) selecting a progeny plant comprising said recombinant introgression.

2. The method of claim 1, wherein selecting the progeny plant comprises identifying a progeny plant that (1) comprises a *Solanum chilense* allele at a locus genetically linked to locus NSLYC008383071 (SEQ ID NO: 1) and/or lacks an allele present at the corresponding locus in the tomato plant, and (2) lacks a *Solanum chilense* allele at a locus genetically linked to locus NSLYC009077970 (SEQ ID NO: 2) that confers necrosis, and/or comprises an allele present at the corresponding locus from in the tomato plant.

3. The method of claim 2, wherein selecting said progeny plant comprises marker-assisted selection (MAS).

4. The method of claim 3, wherein marker-assisted selection (MAS) comprises detecting at least one allele at a locus selected from the group consisting of NSLYC005134429 (SEQ ID NO:3), NSLYC009077970 (SEQ ID NO:2), NSLYC009418370 (SEQ ID NO:4), NSLYC008383071 (SEQ ID NO:1), NSLYC008382908, and NL231193.

5. The method of claim 1, wherein the progeny plant is an F2-F6 progeny plant.

6. The method of claim 1, wherein producing the progeny plant comprises backcrossing.

7. The method of claim 6, wherein backcrossing comprises from 2-7 generations of backcrossing.

8. A method for obtaining a tomato plant exhibiting improved resistance to tomato yellow leaf curl virus, said method comprising:
   (a) obtaining a tomato plant heterozygous for *Solanum chilense* DNA at locus NSLYC008383071 (SEQ ID NO: 1) that confers resistance to tomato yellow leaf curl virus and that is genetically linked in the plant to *Solanum chilense* DNA at locus NSLYC009077970 (SEQ ID NO: 2) that confers necrosis;
   (b) obtaining progeny of the plant; and
   (c) selecting at least a first progeny plant in which recombination has occurred such that the progeny comprises *Solanum chilense* DNA at locus NSLYC008383071 (SEQ ID NO: 1) that confers resistance to tomato yellow leaf curl virus but not said *Solanum chilense* DNA at locus NSLYC009077970 (SEQ ID NO: 2) that confers necrosis;
   wherein selecting said first progeny plant comprises detecting *Solanum chilense* DNA at a locus selected from the group consisting of NSLYC009418370 (SEQ ID NO:4), NSLYC008383071 (SEQ ID NO:1), and NL231193.

9. The method of claim 8, wherein the progeny plant is an F2-F6 progeny plant.

10. The method of claim 8, wherein producing the progeny plant comprises backcrossing.

11. The method of claim 10, wherein backcrossing comprises from 2-7 generations of backcrossing.

12. The method of claim 8, further comprising:
   (d) selecting against alleles on chromosome 2 associated with necrosis;
   wherein said selecting against comprises selecting against plants comprising a CC allele at marker NSLYC008374675 (SEQ ID NO:5), or an AA allele at marker NSLYC008375578 (SEQ ID NO:6), wherein the presence of said alleles confers necrosis.

13. A method for obtaining a tomato plant exhibiting resistance to necrosis, said method comprising:
   (a) obtaining a tomato plant heterozygous for a first allele that confers resistance to necrosis;
   (b) obtaining progeny of the plant; and
   (c) selecting at least a first progeny plant in which recombination has occurred such that the progeny comprises said first allele that confers resistance to necrosis;

wherein selecting said first progeny plant comprises detecting at least one allele at a locus selected from the group consisting of marker NSLYC008374675 (SEQ ID NO:5) and marker NSLYC008375578 (SEQ ID NO:6), wherein said alleles confer a lack of or resistance to necrosis.

14. The method of claim 8, further comprising:
(d) selecting a further progeny plant from among the plants selected in step (c) or subsequent progeny thereof in which a further recombination has occurred between locus NSLYC009418370 (SEQ ID NO:4) and locus NL231193.

15. The method of claim 8, wherein selecting comprises identifying the progeny plant as lacking one or more trait selected from of necrosis, reduced fruit set, and reduced fruit size relative to a plant in which the recombination has not occurred.

* * * * *